United States Patent
Perella et al.

(10) Patent No.: US 6,531,443 B2
(45) Date of Patent: Mar. 11, 2003

(54) ALKANOLAMIDES

(75) Inventors: James E. Perella, Mahwah; Joseph A. Komor, Ramsey; Dennis L. Fost, Ridgewood, all of NJ (US); Richard D. Katstra, Warwick, NY (US)

(73) Assignee: Mona Industries, Inc., Paterson, NJ (US)

( * ) Notice: Subject to any disclaimer, the term of this patent is extended or adjusted under 35 U.S.C. 154(b) by 0 days.

(21) Appl. No.: 09/793,042

(22) Filed: Feb. 26, 2001

(65) Prior Publication Data

US 2001/0044405 A1 Nov. 22, 2001

Related U.S. Application Data

(63) Continuation of application No. 09/334,812, filed on Jun. 17, 1999, now abandoned, which is a continuation-in-part of application No. 09/038,736, filed on Mar. 11, 1998, now abandoned.

(51) Int. Cl.$^7$ ................................................. C11D 3/32
(52) U.S. Cl. ...................... 510/501; 510/506; 554/149; 568/618
(58) Field of Search ................... 554/149, 64; 510/501, 510/506; 568/616, 620, 618

(56) References Cited

U.S. PATENT DOCUMENTS 4,307,079 A * 12/1981 Zorayan et al. ............... 424/70

FOREIGN PATENT DOCUMENTS

| DE | 2643804 A | 4/1978 |
|---|---|---|
| JP | 4-136289 | 5/1992 |
| JP | 8-337560 | 12/1996 |
| WO | WO 95/32942 | * 12/1995 |

* cited by examiner

*Primary Examiner*—John Hardee
(74) *Attorney, Agent, or Firm*—Polly E. Ramstad (57) ABSTRACT

Improved modified monoethanolamide composition mixtures are provided which may be represented by the formula

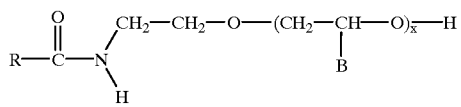

Wherein:

R is an optionally substituted or unsubstituted, branched or straight chain, saturated or unsaturated hydrocarbon radical of 3–21 carbon atoms;

B is $CH_3$ or $-CH_2-CH_3$; and x is at least about 1.

wherein the modified monoethanolamide compositions, which are liquid at ambient temperatures or lower, exhibit surfactant properties substantially the same as those exhibited by diethanolamides such as foam stabilization and viscosity building as well as other desirable characteristics.

24 Claims, 2 Drawing Sheets

ALKANOLAMIDES

RELATED APPLICATION

This application is a continuation of application Ser. No. 09/334,812, filed on Jun. 17, 1999 now abandoned.

This application is a continuation-in-part of application Ser. No. 09/038,736 filed Mar. 11, 1998 abandoned.

FIELD OF THE INVENTION

The present invention relates to improved alkanolamide surfactants and, more particularly, to modified monoethanolamides which are liquid at ambient temperatures and lower and to the method of making the same.

BACKGROUND OF THE INVENTION

Nonionic surfactants are well known and have achieved fast growing commercial importance. They encompass a broad range of compounds having a diverse range of structures and applications. One type of nonionic surfactants are alkanolamides that are condensates, for example, of fatty acids with alkanolamines such as monoethanolamine (MEA), diethanolamine (DEA) and monoisopropanolamine (MIPA), have been used in a variety of cosmetic, personal care, household and industrial formulations.

Alkanolamides are widely used in generally liquid systems such as liquid detergents and personal care products as foam stabilizers, viscosity builders, solubilizers and the like, in metal working formulations as lubricants, viscosity control agents, corrosion inhibitors and in a variety of other applications. Alkanolamides utilized as components in such systems are ethanolamides and/or isopropanolamides such as monoethanolamides, diethanolamides and isopropanolamides in which the fatty acid acyl radical typically contains from 8 to 18 carbon atoms. Such dialkanolamides are typically liquid, while monoalkanolamides are solids having melting points of 40° C. to about 90° C. Heretofore, especially satisfactory alkanolamides have been diethanolamides such as those derived from coconut oil mixed fatty acids or special fractions containing, for instance, predominately $C_{12}$ to $C_{14}$ fatty acids. These alkanolamides are generally liquid in form which greatly simplifies their use. For most applications, alkanolamides prepared from trialkylglycerides are considered most practical due to lower cost, ease of manufacturing and acceptable quality.

Up to now, monoalkanolamides have not been available in liquid form which has limited their use in many applications. In recent years, because of regulatory concerns and restrictions, formulation trends have been shifting toward greater usage of monoalkanolamides; such products being solids, are more difficult to handle and are inconvenient to use in large scale production processes. Accordingly, it would be highly advantageous to be able to combine the performance characteristics of monoethanolamides with products having liquid physical characteristics at below ambient conditions.

Another well known basic group of nonionic surfactants are the alkoxlated derivatives, primarily represented by polyethoxylated and polypropoxylated compounds which are widely used as emulsifiers and detergents but do not provide the advantages of alkanolamides in connection with, for example, foam stabilization and viscosity building. Attempts have been made in the past to use ethylene oxide as an adduction agent for alkanolamides to modify the properties of the alkanolamides in a favorable manner including possibly reducing the congealing temperature of the monoethanolamides. While ethylene oxide adducts of monoethanolamides were found to effect compositions with some modified congealing temperature properties, the amount of ethylene oxide needed to achieve such property changes in the monoethanolamides resulted in products having performance properties which more closely resembled those exhibited by polyoxyethylene compounds, and these derivatives did not retain many of the surfactant characteristics of alkanolamides which were most desirable.

SUMMARY OF THE INVENTION

It is accordingly an object of the present invention to provide a process for preparing modified monoethanolamide surfactant compositions having a congealing temperature less than about 15° C., that preferably are liquids at ambient temperature and lower (e.g. 15° C. or lower), and that exhibit the foam stabilizing, viscosity building and other desirable surfactant characteristics of unmodified dialkanolamide and monoalkanolamide surfactants.

It is another object of the present invention to provide a novel process for preparing an improved monoethanolamide surfactant composition by reacting a monoethanolamide surfactant composition having a congealing temperature of about 40° C. or higher with an amount of propylene or butylene oxide sufficient to prepare a modified monoethanolamide surfactant composition having a congealing temperature of about 15° C. or lower that substantially exhibits the surfactant characteristics of dialkanolamide surfactant compositions and the monoethanolamide reactant.

It is a further object of the present invention to provide improved modified monoethanolamide surfactant compositions having a congealing temperature lower than about 15° C., that preferably is liquid at below ambient temperature and that exhibit foam stabilizing, viscosity building and the like characteristics of dialkanolamide and monoalkanolamide surfactants.

It is still a further object to provide cosmetic and other personal care preparations containing modified monoethanolamide surfactants having congealing temperatures of about 15° C. or lower.

It is yet another object of the present invention to provide metal working and other compositions for a variety of household and industrial applications containing modified monoethanolamide surfactants having congealing temperatures of about 15° C. or lower.

These and other objects will become apparent from the description to follow.

In accordance with the present invention there has now been discovered a novel process for preparing monoethanolamide surfactant compositions having congealing temperatures of about 15° C. or lower which comprises:

a) providing a monoethanolamide composition mixture derived from triglyceride oils and fats represented by the formula wherein:

R is an optionally substituted or unsubstituted, branched or straight chain, saturated or unsaturated hydrocarbon radical of 3–21 carbon atoms; and b) reacting said monoethanolamide composition mixture in the presence of a suitable catalyst with an amount of propylene oxide, butylene oxide or mixtures of the same sufficient to form a modified monoethanolamide surfactant composition mixture that is liquid at below ambient temperature, preferably having a congealing temperature of about 15° C. or lower. In general, the reaction is carried out for a time sufficient for substantially all of the alkylene oxide to react.

In another aspect of the present invention there are provided modified monoethanolamide surfactant composition mixtures having a congealing temperature of about 15° C. or lower the predominant component of which is a modified monoethanolamide represented by the formula Wherein:
R is an optionally substituted or unsubstituted, branched or straight chain, saturated or unsaturated hydrocarbon radical of 3–21 carbon atoms;
B is $CH_3$ or $—CH_2—CH_3$; and
x is an average value of at least about 1 representing the ratio of moles of alkylene oxide selected from propylene oxide, butylene oxide and mixtures thereof to moles of monoethanolamide sufficient to prepare a monoethanolamide composition mixture having a congealing temperature of 15° C. or lower.

Other components in such mixtures, are alkoxylated glycerin, glycerin and nonalkoxylated monoethanolamide the total amount of which generally ranges from 10% to about 55% by weight, the relative concentration of each of such additional components depending on the degree of alkoxylation of the reaction mixture and the monoethanolamide composition mixture from which the modified monoethanolamide composition mixture of the invention is prepared.

The modified monoethanolamide composition mixtures of the present invention which are liquids at lower than ambient temperature, preferably have a congealing temperature of about 15° C. or, most preferably lower, surprisingly and unexpectedly generally exhibit most, if not all, of the surfactant characteristics of dialkanolamide surfactant compositions such as the foam stabilization and viscosity building properties, as well as retaining substantially all the favorable properties of the monoethanolamides from which the compositions are prepared.

In yet another aspect of the present invention, there are provided cosmetic and personal care compositions which comprise at least 0.1% by weight of a modified monoethanolamide surfactant composition mixture which is liquid at lower than ambient temperature, the predominant component of which is a modified monoethanolamide that may be represented by the formula Wherein:
R is an optionally substituted or unsubstituted, branched or straight chain, saturated or unsaturated hydrocarbon radical of 3–21 carbon atoms;
B is $CH_3$ or $—CH_2—CH_3$; and
x has an average value of at least about 1 as hereinabove defined.

In a still further aspect of the present invention there are provided metal working compositions and household cleaning products which are in liquid form comprising at least 0.1% by weight of a modified monoethanolamide surfactant composition mixture which is a liquid at lower than ambient temperature, the predominant component of which is a modified monoethanolamide that may be represented by the formula Wherein:
R is an optionally substituted or unsubstituted, branched or straight chain, saturated or unsaturated hydrocarbon radical of 3–21 carbon atoms;
B is $CH_3$ or $—CH_2—CH_3$; and
x is hereinabove defined.

DESCRIPTION OF THE PREFERRED EMBODIMENTS

In accordance with the present invention, materials and methods are provided which enhance the properties of a well known and widely used class of nonionic surfactant compositions making an easily handleable group thereof readily and economically available for use in a variety of cosmetic, personal care, household and industrial applications.

The method of this invention applies to the treatment of a monoethanolamide surfactant composition mixture generally having a congealing temperature of about 40° C. or higher by reacting a normally solid monoethanolamide composition mixture prepared from triglyceride oils or fats in the presence of a suitable catalyst, preferably potassium hydroxide or sodium alcoholate, with an amount of butylene oxide or preferably propylene oxide only sufficient to prepare a monoethanolamide derivative composition mixture which is liquid at lower than ambient temperatures (about 20° C.) and preferably has a congealing temperature of about 15° C. or lower. The monoethanolamide derivative composition mixtures which are prepared in accordance with the practice of the present invention exhibit surfactant properties such as foam stabilization and viscosity building as well as other desirable characteristics which are similar to those exhibited by dialkanolamides and are substantially the same as those provided by the unmodified monoethanolamide composition mixtures. Moreover, the monoethanolamide derivative composition mixtures of the present invention which are liquid at lower than ambient temperatures, are not known to have any undesirable toxicological or environmental concerns.

In general, the method of the present invention can be accomplished by treating a monoethanolamide composition mixture derived from triglyceride fats and oils having the formula wherein:
R is an optionally substituted or unsubstituted, branched or straight chain, saturated or unsaturated hydrocarbon radical of 3–21, preferably 7–17 carbon atoms;
with an amount of propylene oxide, butylene oxide or mixtures of the same in the presence of a suitable catalyst, such as potassium hydroxide, sodium alcoholate and the like, that is only sufficient to form a monoethanolamide derivative composition mixture which is liquid at ambient temperatures or lower and, preferably, substantially retains the surfactant characteristics of the unmodified monoethanolamide composition.

Figure 1:
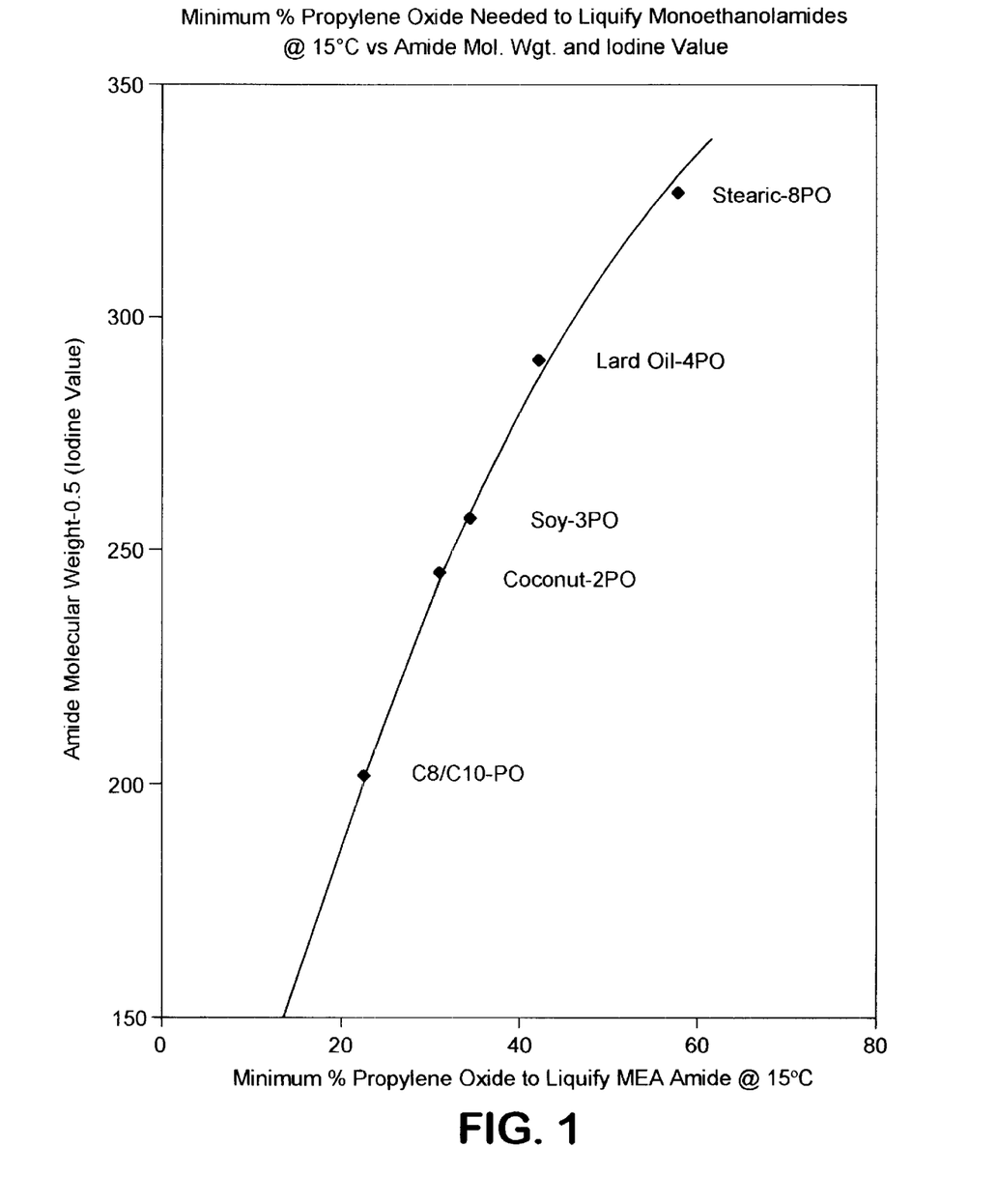
FIG. 1 is a graph illustrating the quantity of propylene oxide to be reacted with various triglyceride-derived monoethanolamide compositions.

The reaction of the monoethanolamide composition mixture with propylene oxide, butylene oxide or mixtures of the same for adding one or more moles of propylene oxide, butylene oxide or mixtures of the same onto the alkanolamide containing mixture in accordance with the invention can be carried out using any well known method. The degree of alkoxylation of the monoethanolamide composition mixture being treated is important but may be varied depending upon the molecular weight of the monoethanolamide composition component of the mixture and the degree of unsaturation in the fatty alkyl amide moiety as expressed by the iodine value thereof, generally by adding at least about 1 to about 8 moles, preferably from 1 to 4 moles, of propylene oxide, butylene oxide or mixtures thereof, per mole of the monoethanolamide component. However, the number of moles of alkylene oxide used, as indicated, should be only the amount sufficient to produce a monoethanolamide derivative composition mixture which is liquid at lower than ambient temperatures, and, preferably, has a congealing temperature of about 15° C. or, more preferably, lower. In FIG. 1 there is illustrated the minimum quantity of propylene oxide needed to be reacted with various tryglyceride-derived monoethanolamide to achieve products which are liquid at 15° C.

The typically solid monoethanolamide compositions suitable for use in the preparation of modified monoethanolamide composition mixtures of the present invention having a congealing temperature of about 15° C. or preferably lower in accordance with the practice of the present invention are well known and include those derived by known processes from substituted or unsubstituted, branched or straight chain, saturated or unsaturated triglycerides with fatty alkyl amide moieties having from 4 to 22 carbon atoms, preferably having from 8 to 18 carbon atoms. Suitable triglycerides from which the monoethanolamide composition mixtures may be prepared include glyceride esters of acids such as octanoic acid, decanoic acid, lauric acid, myristic acid, palmitic acid, stearic acid, oleic acid, linoleic acid, linolenic acid, or mixtures thereof as are found in coconut oil, palm oil, sunflower oil, soybean oil, rapeseed oil, castor oil, fish oil, tallow fat, milk fat, lard and other natural sources or may be of synthetic origin. As is known, the solid monoethanolamide composition mixtures suitable for use in the preparation of modified monoethanolamide composition mixtures of the present invention, derived from triglycerides, contain mixtures which are predominantly monoethanolamide derivatives of monoethanolamine, e.g. 3 moles, and small amounts of glycerin, e.g. 1 mole. Such monoethanolamide composition mixtures are typically used as prepared without the need for separation of the glycerin component from the monoethanolamide composition.

The modified monoethanolamide surfactant composition mixtures of the present invention which are prepared in accordance with the practice of the present invention contain a predominant monoethanolamide component, preferably at least about 85% by weight, which may be represented by the formula Wherein:
R is an optionally substituted or unsubstituted, branched or straight chain, saturated or unsaturated hydrocarbon radical of 3–21, preferably, 7–17 carbon atoms;
B is —CH$_3$ or —CH$_2$—CH$_3$; and
x has an average value of at least 1 to about 8, preferably from 1 to 4, representing the ratio of moles of alkylene oxide selected from propylene oxide, butylene oxide and mixtures of the same to moles of monoethanolamide component sufficient to prepare a monethanolamide composition mixture having a congealing temperature of 15° C. or lower.

As indicated, the monoethanolamide composition mixtures which are typically high temperature melting waxy solids that are converted into the monoethanolamide derivative composition mixtures of the present invention may be prepared in a suitable manner by well known processes preferably from triglyceride oils and fats wherein the resulting product includes a glycerin component. The modified monoethanolamide surfactant composition mixtures of the present invention, which are liquids at ambient temperatures and, preferably, have a congealing temperature of about 15° C. or lower, surprisingly and unexpectedly retain the generally useful and desirable surfactant and other properties of the monoethanolamide composition mixtures from which they are prepared as well as those exhibited by diethanolamide compositions that are well known and widely used. The monoethanolamide composition mixtures of the present invention include other components such as alkoxylated glycerin, glycerin and non-alkoxylated monoethanolamide, the total amount of which is the modified monoethanolamide composition mixtures may range from about 10% to 50% by weight of the compositions.

Figure 2:
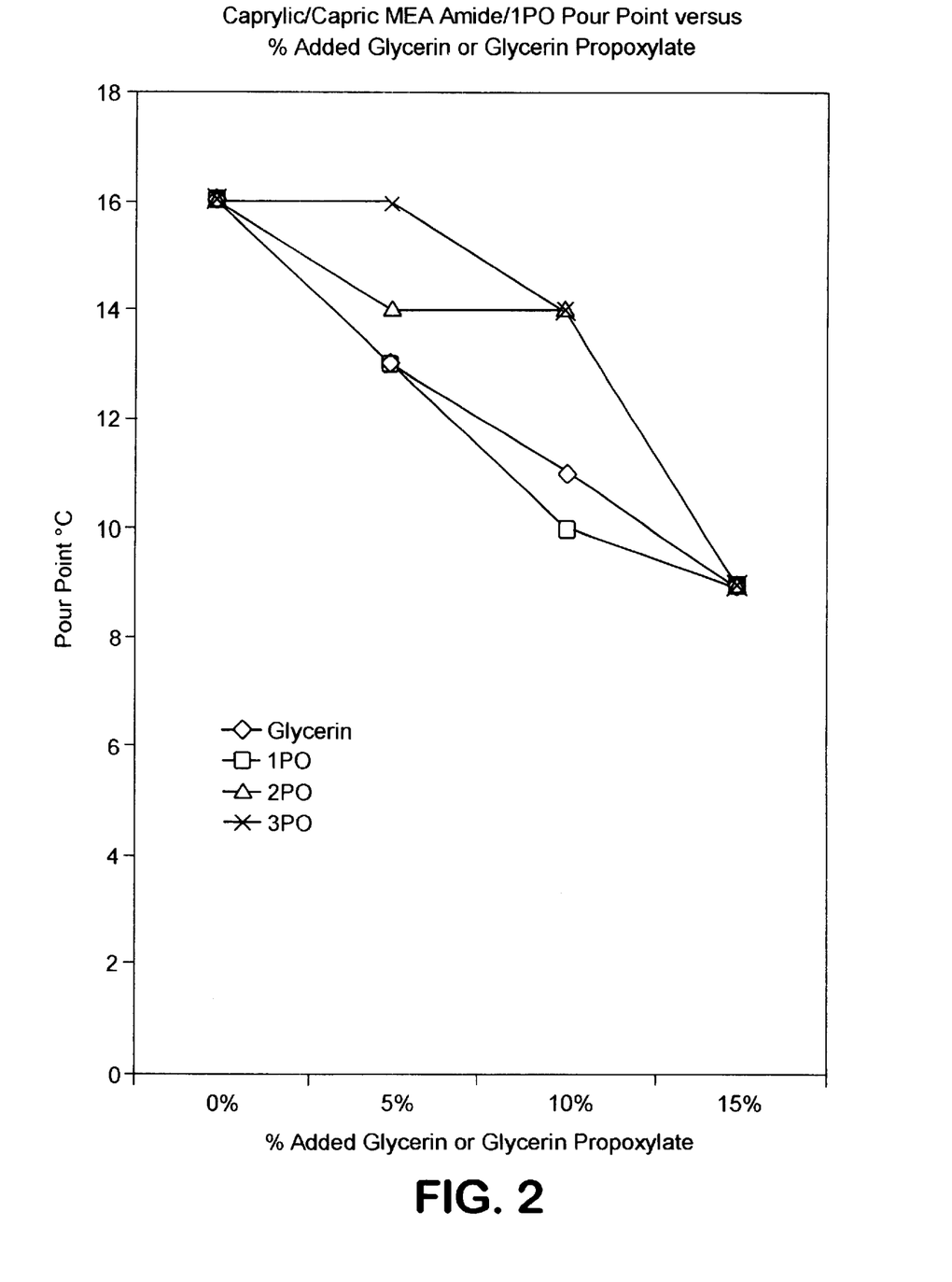
FIG. 2 is a graph-illustrating the effect of added glycerin or glycerin propoxylates on the pour point properties of a triglyceride-derived caprylic/capric monoethanolamide modified with 1 mole of propylene oxide.

The effect of added glycerin or glycerin propoxylates on the pour point of a triglyceride-derived caprylic/capric monethanolamide modified with 1 mole of propylene oxide (such as in Example 4) is shown in FIG. 2. Increased liquidity is achieved by increased concentrations of the same glycerin and propoxylated glycerin components already contained in the product such as disclosed in Example 4, indicating that these components exhibit an added liquefying effect that goes beyond that of the propoxylated amide when used alone.

The following Table 1 presents compositional analyses of three propoxylated products of differing alkyl chain lengths prepared from triglycerides and such as detailed in Examples 1, 3A and 4. The relative percentages of ingredients in the modified monoethanolamide mixtures are dependent upon the composition of the triglyceride derived monoethanolamide mixtures used as a reactant and the corresponding necessary degree of alkoxylation (propoxylation) to achieve congealing temperatures of 15° C. or lower. Theoretically determined values and actual analyses show good overall agreement. All of the products prepared from triglycerides result in mixtures that are predominantly alkoxylated monoethanolamides and alkoxylated glycerin but those products derived from short alkyl chain triglycerides, such as in Example 4, also contain significant percentages of unreacted monoalkanolamide. In all cases the broad product mixtures result in compositions that display excellent low temperature congealing temperatures and performance characteristics similar to unmodified mono- and dialkanolamide surfactants and represent compositions of matter totally distinct from products such as disclosed, for example, in Japanese Kokai Patent No. Hei 8-337560 applied for by Kawaken Fine Chemicals Co., Ltd. The surfactants in this Kawaken application are not derived from triglyceride oils/fats and they do not contain any glycerin or glycerin alkoxylates which contribute to low temperature fluidity characteristics.

TABLE 1

Composition of Modified Monethanolamides
% By Weight

| Componenets | Example 4 Caprylic/Capric MEA Amide-1PO | | Example 1 Coconut MEA Amide-2PO | | Example 3A Soya MEA MEA Amide-3PO | |
|---|---|---|---|---|---|---|
| | Theory | Found | Theory | Found | Theory | Found |
| Propoxylated Amide | 44.6 | 46.9 | 77.7 | 68.9 | 77.7 | 75.5 |
| Non-Propoxylated Amide | 34.4 | 32.1 | 0.0 | 8.8 | 0.0 | 2.2 |
| Propoxylated Glycerin | 21.0 | 18.7 | 22.3 | 20.7 | 22.3 | 22.3 |
| Glycerin | 0.0 | 2.3 | 0.0 | 1.6 | 0.0 | 0.0 |

The degree of alkoxylation, that is, the number of groupings "x" of the above formula, may be varied but only within narrow limits. Monoethanolamide derivative composition mixtures of the invention which are adducts of only a sufficient amount of butylene oxide or, preferably, propylene oxide per mole of monoethanolamide and glycerine in the mixture, generally from at least about 1 to about 8 moles, preferably from 1–4 moles, of alkylene oxide, surprisingly and unexpectedly are liquids at lower than ambient temperatures and preferably have a congealing temperature of about 15° C. or lower while advantageously retaining the desirable surfactant characteristics of the unmodified monoethanolamide composition mixtures as well as displaying the surfactant properties of diethanolamides. Depending on the molecular weight and degree of unsaturation of the fatty alkyl amide moiety of the monoethanolamide composition component as expressed by the iodine value (I.V.) thereof, the monoethanolamide derivative composition mixtures of the present invention will contain an amount of propylene oxide to monoethanolamide derivative component of the composition mixture in the range from at least 15% by weight to about 57% by weight, or an amount of butylene oxide to monoethanolamide derivative composition in the range from about 40% by weight to 60% by weight. In the case of monoethanolamlde composition mixtures containing saturated high molecular weight amide moieties (iodine values of about 0, e.g. stearyl derivatives), at least 60% by weight of butylene oxide and/or propylene oxide or higher is required to liquify such derivatives below ambient temperatures.

The novel modified monoethanolamide composition mixtures of the invention surprisingly and unexpectedly display many of the well known properties of diethanolamides such as foam stabilization and viscosity building as well as other desirable properties such as emulsification of oil based materials, solubilization of fragrances and hair colorants and dyes, wetting of natural and synthetic fibers, compatability with anionic surfactants and detergents and the like while exhibiting congealing temperatures which are substantially lower than those of the unmodified monoethanolamide compositions, thus making them easy to formulate into a wide range of cosmetic, personal care, household and industrial systems. In contrast thereto, reactions which involve treating typically solid monoethanolamide compositions with 5 or more moles of ethylene oxide in the presence of a suitable catalyst are useful in forming derivatives thereof which are flowable solids or gels at ambient temperatures (20–25° C.) but the monoethanolamide derivatives thus formed, significantly lack many of the desirable alkanolamide surfactant properties such as foam stabilization and viscosity building.

It is therefore a further aspect of the invention to use the novel compositions of the invention, for example, in cosmetic preparations and the like, especially in preparations for hair care and skin treatment. In this connection, personal care formulations can be shampoos, hair colorants, hair conditioners, bath products and skin treatment cremes and lotions. Other formulations where the properties of the novel compositions of the invention can be utilized include make-up cremes, sunscreens, lipstick, pressed powders, skin-toners, antiperspirants and the like. Shampoos to which the novel modified monoethanolamide compositions of the invention have been added in amounts of from 0.1 to 10 percent by weight or greater and which contain up to about 30 weight percent of substances with detergent activity, in addition to water and possibly other ingredients, result in compositions having desired foam stability and viscosity building as well as many other desirable characteristics.

Conventional additives such as perfumes, preservatives, complexing agents, opacifiers, luster developing agents and the like may be added to any of the above mentioned personal care products.

The novel modified monoethanolamide composition mixtures may also be added to a wide variety of home care and industrial formulations wherein their usefulness as detergents, metal working and lubricating agents, emulsifiers, anticorrosion agents for metal products and various other liquid and/or water based personal care, home care and industrial compositions wherein diethanolamide and unmodified monoethanolamide compositions have been found useful. The preparation of specific compositions of the invention is illustrated by the following examples which are provided herein for purposes of illustration only and are not intended to limit the scope thereof.

EXAMPLE 1

A three-necked flask fitted with an agitator, thermometer, dry-ice condenser, heating mantle and addition funnel is charged with 125 grams of a solid commercially available coconut monoethanolamide having the tradename MONAMID CMA, which is prepared from coconut oil and monoethanolamine and contain 10.9% of free residual glycerine. The solid monoethanolamide (congealing temperature 63° C.; Iodine Value (I.V.)-9) is melted at 70–80° C., 0.9 grams of 85% potassium hydroxide catalyst are added and the mixture is stirred until homogeneous. The temperature of the reaction mixture is raised to 140–150° C. and 58 grams of propylene oxide is added dropwise over a period of 1.5 hours. The reaction mixture is stirred at 140–150° C. for an additional hour after which it is cooled to 25° C. The propoxylated monoethanolamide product mixture with a propylene oxide content of 31.5% by weight is a clear amber liquid having a congealing temperature of –1° C.

EXAMPLE 2

A) Using the reaction vessel and procedure of example 1, a propoxylated monoethanolamide mixture is prepared from 125 grams of the coconut monoethanolamide material of example 1 except that only 29 grams of propylene oxide is added to the heated monoethanolamide reactant. After completion of the reaction, the product with a propylene oxide content of 18.7% by weight is cooled to 25° C. and a nonclear pasty liquid results.

B) Using the reaction vessel and procedure of example 1, a propoxylated monoethanolamide is prepared from 125 grams of the coconut monoethanolamide material of example 1 except that 174.3 grams of propylene oxide is added to the heated monoethanolamide reaction mixture. After completion of the reaction and cooling, a reaction product with a propylene oxide content of 58.1% by weight which is a clear amber liquid is obtained.

C) Using the reaction vessel and procedure of example 1, a propoxylated monoethanolamide mixture is prepared from 125 grams of the coconut monoethanolamide material of example 1 except that 232.4 grams of propylene oxide is added to the heated monoethanolamide reaction mixture. After completion of the reaction and cooling, a clear dark amber liquid reaction product is obtained having a propylene oxide content of 64.9% by weight.

EXAMPLE 3

A) Using the reaction vessel of example 1, 192.6 grams of a soya monoethanolamide mixture (tan solid—congealing temperature 45° C.; Iodine Value—130) prepared from soybean oil and monoethanolamine is charged into the reactor and heated at 70–80° C. together with 1.5 grams of flake 85% potassium hydroxide. The mixture is agitated until homogeneous and the temperature is then raised to 140–150° C. While maintaining the temperature with agitation, 104.6 grams of propylene oxide is added dropwise over a period of 2.5 hours. The reaction mixture is stirred for an additional hour at 140–150° C. and then cooled to 25° C. After cooling, the reaction product with a propylene oxide content of 35.0% is a clear amber liquid having a congealing temperature of –1° C.

B) The reaction of A) above is run except that only 69.76 grams of propylene oxide is added dropwise to the molten soya monoethanolamide reactant. The resultant product having a propylene oxide content of 26.4% is a paste at 25° C.

EXAMPLE 4

Using the reaction vessel of example 1, 230.1 grams of a caprylic/capric monoethanolamide mixture(I.V.—0) prepared from a $C_8/C_{10}$ triglyceride and monoethanolamine is charged into the reactor with 1.5 grams of 85% flake potassium hydroxide and heated at 70–80° C. with agitation until a homogeneous mixture is formed. The temperature of the reaction mixture is then raised to 140–150° C. and 68.4 grams of propylene oxide is added dropwise over a period of 1.5 hours. The reaction mixture is stirred for another hour at a temperature of 140–150° C. The reaction product with a propylene oxide of 22.8% by weight is a clear amber liquid at 20° C.

EXAMPLE 5

A) using the reaction vessel of example 1, 125 grams of the solid coco monoethanolamide of example 1 is charged into the reaction vessel and melted at 70–80° C. at which time 0. 9 grams of 85% potassium hydroxide is added and the mixture is stirred until homogeneous. The temperature of the reaction mixture is raised to 140–150° C. and 108 grams of butylene oxide are added dropwise to the reaction mixture with stirring over a period of 1.5 hours. The reaction mixture is maintained at 140–150° C. with stirring for an additional hour, after which it is cooled to 25° C. The reaction product with a butylene oxide content of 46.2% is a clear amber liquid.

B) The reaction of A) above is run except that only 72 grams of butylene oxide are added dropwise to the coco alkanolamide reaction mixture over a period of 2.5 hours. After cooling, the reaction product having a butylene content of 36.4% is a solid.

C) The reaction of A) above is run except that 180 grams of butylene oxide are added dropwise to the coco alkanolamide reaction mixture over a period 2.5 hours. After cooling, the reaction product with a butylene oxide content of 59% is a clear amber liquid.

EXAMPLE 6

The propoxylated monoethanolamide derivative compositions of examples 1, 3A and 4 are used in this example. Foam stabilization properties of various modified monoethanolamide composition mixtures are evaluated and the properties effected by the monoethanolamide derivative composition mixtures (all having congealing temperatures less than 15° C.) of the present invention are compared with those obtained with a commercial diethanolamide composition, an unmodified monoethanolamide mixture (solid with a congealing temperature of 63° C.) and a commercial monoethanolamide reacted with 5 moles of ethylene oxide (congealing temperature 25° C. The results of the tests are reported below in Table 2.

TABLE 2

| | Ross Miles Foam Test (mm of Foam) | | |
|---|---|---|---|
| Sample Tested | At 0 Minutes | After 1 Minute | After 5 Minutes |
| Example 1 Comp. | 230 | 201 | 197 |
| Unmodified Coconut monoethanolamide MONAMID CMA | 231 | 206 | 201 |
| Example 3A Comp. | 236 | 212 | 206 |
| Example 4 Comp. | 233 | 208 | 203 |
| Coconut Diethanolamide | 234 | 204 | 201 |
| Coconut Monoethanolamide + 5 moles of Ethylene Oxide | 135 | 119 | 15 |

The test is run according to ASTM Method D1173-53 with 19% of Sodium Lauryl Sulfate + 1% test amide. 0.1% total active in 0 ppm water hardness, temperature = 25° C.

As can be seen, the monoethanolamide derivative composition mixtures with low levels of propoxylation, which are liquids, exhibit excellent foam stabilization properties when blended with an anionic surfactant, such as sodium lauryl sulfate, substantially the same as the foam stablization characteristics of coconut diethanolamide and unmodified coconut monoethanolamide mixture. In contrast thereto, an ethylene oxide adduct of the coconut monoethanolamide is not liquid and does not stabilize foam.

EXAMPLE 7

The propoxylated monoethanolamide derivative composition mixtures of examples 1, 3A and 4 are used in this example. Viscosity building properties of various monoethanolamide derivative composition mixtures of the invention are evaluated and compared with the properties effected by a commercial diethanolamide composition (congealing temperature −4° C.), an unmodified monoethanolamide (solid-congealing temperature 63° C.) and a commercial monoethanolamide adducted with 5 moles of ethylene oxide (congealing temperature 25° C.). The results are reported below in Table 3.

TABLE 3

Viscosity Comparisons of Sodium Lauryl Sulfate Blends

| Sample Tested | Viscosity (cPs) 1% Added NaCl |
| --- | --- |
| Example 1 Comp. | 283 |
| Unmodified Coconut monoethanolamide MONAMID CMA | 625 |
| Example 3A Comp. | 120 |
| Example 4 Comp. | 130 |
| Coconut Diethanolamide | 173 |
| Coconut Monoethanolamide + 5 moles of Ethylene Oxide | 45 |

Test Formulation: 19% of Sodium Lauryl Sulfate active + 1% test sample.

While the propoxylated monoethanolamide compositions (Examples 1, 3A and 4 Compositions) exhibit somewhat reduced viscosity building characteristics compared to an unmodified coconut monoethanolamide composition mixture, they are approximately equivalent in viscosity building to a coconut diethanolamide composition and are clearly superior to the ethylene oxide adduct of a coconut monoethanolamide.

EXAMPLE 8

The alkoxylated monoethanolamide derivative compositions of examples 1, 2B and 2C are used in this example. Prototype hair shampoo formulations are prepared using 15% active sodium lauryl sulfate and 3% active monoethanolamide derivative compositions. A shampoo sample is prepared for comparison purposes from a solid commercially available fatty acid derived monoethanolamide having the Trade Name MONAMID CMA-A. The various shampoo samples are evaluated for Ross-Miles Foam and Viscosity and the results are reported in Table 4, below.

TABLE 4

| | Sample Tested | | | |
| --- | --- | --- | --- | --- |
| | CMA-A | Comp 1 | Comp 2B | Comp 2C |
| Ross-Miles Foam (mm) | | | | |
| initial | 185 | 205 | 180 | 177 |
| 1 min. | 170 | 179 | 155 | 152 |
| 5 min. | 165 | 172 | 147 | 142 |
| Viscosity (cP) | | | | |
| No Salt | 25 | 16 | 4 | 6 |
| 1% NaCl | | 440 | 7.5 | 5 |

As can be seen, the monoethanolamide derivative composition mixture with a low level of propoxylation (example 1) which is liquid, exhibits excellent foam stabilization properties when blended with an anionic surfactant, such as sodium lauryl sulfate, substantially the same as the foam stablization characteristics of unmodified coconut monoethanolamide which is not a liquid. In contrast thereto, the coconut monoethanolamide derivative compositions with high levels of propylene oxide, example 2B and 2C compositions, do not stabilize foam as effectively. Moreover, the propoxylated monoethanolamide composition mixtures with a low level of propylene oxide (Example 1) which is a liquid, exhibits significant viscosity building characteristics, whereas the propoxylated monoethanolamide composition mixtures with high level of propylene oxide, example 2B) and 2C) compositions, exhibit poor viscosity building characteristics.

EXAMPLE 9

The alkoxylated monoethanolamide derivative composition mixtures of example 1 is used in this example. Cotton wetting by the monoethanolamide derivative composition mixtures of the invention are evaluated and compared to the wetting characteristic of the unmodified monoethanolamide composition of example 1. The results are reported in Table 5, below.

TABLE 5

Draves Cotton Skein Wetting Test

Concentration: 0.1% active in deionized water*
Temperature: 25° C.
Method: AATCC 17-1994

| Cotton Skein Wetting Time | |
| --- | --- |
| Unmodified Coconut Monoethanolamide Triglyceride-Derived | Composition of Example 1 |
| Test terminated with no wetting after 2,100 seconds | Wets at 39.0 seconds |

*Note: The propoxylated alkanolamide composition mixture of example 1 is noted to be more easily dispersible and soluble than the unmodified alkanolamide composition.

As can be seen, the wetting characteristics of the liquid modified monoethanolamide composition mixtures of the invention, which is readily soluble and/or dispersible in water, is clearly superior to the wetting characteristics of a solid unmodified monoethanolamide composition.

It will be evident from the above that there are other embodiments and methods, which while not expressly described above, are clearly within the scope and spirit of the invention. The description above is therefore intended to be exemplary only and the scope of this invention is to be limited solely by the appended claims.

What is claimed is:

1. A method for preparing a modified monoethanolamide surfactant composition having a congealing temperature of lower than ambient temperature which comprises:

a) providing a monethanolamide composition derived from triglyceride oils and fats represented by the formula wherein:

R is an optionally substituted or unsubstituted, branch or straight chain, saturated or unsaturated hydrocarbon radical of 3–21 carbon atoms; and b) reacting said monoethanolamide composition in the presence of a suitable catalyst with an effective amount of propylene oxide, butylene oxide or combinations thereof sufficient to achieve said congealing temperature.

2. The method as claimed in claim 1, wherein said monoethanolamide composition is reacted with from 1 to 8 moles of propylene oxide, butylene oxide or combinations thereof.

3. The method as claimed in claim 1, wherein said monoethanolamide composition is reacted with from 1 to about 4 moles of propylene oxide.

4. The method as claimed in claim 1, wherein said monoethanolamide composition of step (a) has a congealing temperature of at least about 40° C.

5. The method of claim 1, wherein said congealing temperature is about 20° C. or lower.

6. The method of claim 1, wherein said congealing temperature is about 15° C. or lower.

7. A method for preparing a modified monoethanolamide surfactant composition substantially liquid at ambient temperature or lower which comprises:

a) providing a monethanolamide composition derived from triglyceride oils and fats represented by the formula wherein:

R is an optionally substituted or unsubstituted, branched or straight chain, saturated or unsaturated hydrocarbon radical of 3–21 carbon atoms; and b) reacting said monoethanolamide composition in the presence of a suitable catalyst with an amount of propylene oxide, butylene oxide or combinations thereof, sufficient to render said modified monoethanolamide substantially liquid at ambient temperature.

8. A modified monoethanolamide surfactant composition comprising a component of the formula wherein R is an optionally substituted or unsubstituted, branched or straight chain, saturated or unsaturated hydrocarbon radical of 3–21 carbon atoms;

B is —$CH_3$ or —$CH_2$—$CH_3$;

x has an average value of at least 1 representing the ratio of moles of alkylene oxide selected from propylene oxide, butylene oxide and combinations thereof to moles of monoethanolamide compound sufficient to prepare a monoethanolamide composition mixture having a congealing temperature lower than ambient temperature;

and being suitable to exhibit foam stabilization and viscosity building properties; and further comprising glycerine.

9. The composition of claim 8, wherein said glycerine is alkoxylated with an alkylene oxide selected from the group consisting of propylene oxide, butylene oxide, and combinations thereof.

10. The composition of claim 8 wherein said glycerine comprises from about 10% to about 55% by weight of said composition.

11. The composition of claim 8 wherein said glycerine comprises from about 15% to about 25% by weight of said composition.

12. The composition of claim 8 wherein said R is a member selected from the group consisting of a coconut oil hydrocarbon radical, a capric acid hydrocarbon radical, and a soybean oil hydrocarbon radical.

13. The composition of claim 9 wherein said R is a member selected from the group consisting of a coconut oil hydrocarbon radical, a capric acid hydrocarbon radical, and a soybean oil hydrocarbon radical.

14. A modified surfactant composition comprising the reaction product of:

(i) a monoethanolamide comprising the reaction product of a triglyceride and a monoethanolamine; and (ii) an alkylene oxide in an amount sufficient to render said surfactant liquid at ambient temperature or less, said alkylene oxide being selected from the group consisting of propylene oxide, butylene oxide and combinations thereof.

15. The modified surfactant composition as claimed in claim 14 wherein reaction product has the formula wherein R is an optionally substituted or unsubstituted, branched or straight chain, saturated or unsaturated hydrocarbon radical of 3–21 carbon atoms;

B is —$CH_3$ or —$CH_2$—$CH_3$; and x has an average value of at least 1 representing the ratio of moles of alkylene oxide to moles of monoethanolamide compound sufficient to prepare said monoethanolamide composition with a congealing temperature lower than ambient temperature;

said composition being suitable to exhibit foam stabilization and viscosity building properties.

16. The modified monoethanolamide surfactant composition as claimed in claim 15, wherein x is from 1 to 4.

17. The composition of claim 15, wherein said R is a member selected from the group consisting of a coconut oil hydrocarbon radical, a capric acid hydrocarbon radical, and a soybean oil hydrocarbon radical.

18. The modified monoethanolamide surfactant composition of claim 14, wherein said reaction product comprises at least about 44% by weight of said composition.

19. The modified monoethanolamide surfactant composition of claim 18, wherein said reaction product comprises about 44% to about 78% by weight of said composition.

20. The modified monoethanolamide surfactant composition of claim 14, wherein said reaction product comprises at least about 85% by weight of said composition.

21. Cosmetic, personal care and household use compositions which comprise at least 0.1% by weight of a modified surfactant composition comprising the reaction product of:
(i) a monoethanolamide comprising the reaction product of a triglyceride and a monoethanolamine; and
(ii) an alkylene oxide in an amount sufficient to render said surfactant liquid at ambient temperature or less, said alkylene oxide being selected from the group consisting of propylene oxide, butylene oxide and mixtures thereof.

22. The composition of claim 21, wherein said R is a member selected from the group consisting of a coconut oil hydrocarbon radical, a capric acid hydrocarbon radical, and a soybean oil hydrocarbon radical.

23. Metal working and industrial use compositions which are in liquid form comprising at least 0.1% by weight of a modified surfactant composition comprising the reaction product of:
(i) a monoethanolamide comprising the reaction product of a triglyceride and a monoethanolamine; and
(ii) an alkylene oxide in amount sufficient to render said surfactant liquid at ambient temperature or less, said alkylene oxide being selected from the group consisting of propylene oxide, butylene oxide and mixtures thereof.

24. The composition of claim 23, wherein said R is a member selected from the group consisting of a coconut oil hydrocarbon radical, a capric acid hydrocarbon radical, and a soybean oil hydrocarbon radical.

* * * * *